United States Patent
Clarence-Smith

(10) Patent No.: US 11,752,141 B2
(45) Date of Patent: *Sep. 12, 2023

(54) PHARMACEUTICAL COMPOSITIONS AND METHODS UTILIZING NEOSTIGMINE AND AN NK-1 ANTAGONIST FOR TREATING MYASTHENIA GRAVIS

(71) Applicant: DAS-MG, Inc., Boston, MA (US)

(72) Inventor: Kathleen Clarence-Smith, Washington, DC (US)

(73) Assignee: DAS-MG, Inc., Boston, MA (US)

( * ) Notice: Subject to any disclaimer, the term of this patent is extended or adjusted under 35 U.S.C. 154(b) by 335 days.

This patent is subject to a terminal disclaimer.

(21) Appl. No.: 16/752,590

(22) Filed: Jan. 24, 2020

(65) Prior Publication Data

US 2020/0155530 A1 May 21, 2020

Related U.S. Application Data

(63) Continuation of application No. PCT/US2018/043636, filed on Jul. 25, 2018.

(60) Provisional application No. 62/695,462, filed on Jul. 9, 2018, provisional application No. 62/536,595, filed on Jul. 25, 2017.

(51) Int. Cl.
| | | |
|---|---|---|
| *A61K 31/4425* | (2006.01) | |
| *A61P 21/04* | (2006.01) | |
| *A61K 31/5377* | (2006.01) | |

(52) U.S. Cl.
CPC ...... *A61K 31/4425* (2013.01); *A61K 31/5377* (2013.01); *A61P 21/04* (2018.01)

(58) Field of Classification Search
CPC .............. A61K 31/5377; A61K 31/675; A61K 31/495; A61K 31/444; A61K 31/4425; A61K 2300/00; A61K 45/06; A61P 21/04
See application file for complete search history.

(56) References Cited

U.S. PATENT DOCUMENTS

| 2009/0264388 A1* | 10/2009 | Maghni | A61K 31/519 |
| | | | 514/171 |
| 2011/0243924 A1 | 10/2011 | Supervia | |
| 2014/0193526 A1* | 7/2014 | Henry | A61K 31/194 |
| | | | 424/715 |
| 2016/0375001 A1* | 12/2016 | Chase | A61K 31/4178 |
| | | | 514/257 |

FOREIGN PATENT DOCUMENTS

| CN | 105434403 | 3/2016 |
| WO | 2006005017 | 1/2006 |
| WO | 2018129434 | 7/2018 |

OTHER PUBLICATIONS

Maggi et al. Clin Drug Investig, 2011; 31(10): 691-701. (Year: 2011).*
Bangalor et al. "Fixed-dose combinations improve medication compliance: a meta-analysis." 2007, pp. 1-5 (Year: 2007).*
Mestinon Data Sheet. Wayback Machine publicly available date: Oct. 13, 2012. Retrieved on Nov. 4, 2022. Retrieved from the internet <URL: https://web.archive.org/web/20121013115507/https://www.medsafe.govt.nz/profs/datasheet/m/Mestinontab.pdf>; pp. 1-5. (Year: 2012).*
Langford, et al., Fosaprepitant and aprepitant: an update of the evidence for their place in the prevention of chemotherapy-induced nausea and vomiting, Core Evidence, Sep. 24, 2009, vol. 5, pp. 77-90.
Hermann, et al., Myasthenia Gravis and the Myasthenic Syndrome, California Medicine, Sep. 1970, vol. 113, pp. 27-36.
International Search Report for PCT/US2018/43636 dated Oct. 15, 2018.
Abicht A, Muller J S, Lochmiiller H. Congenital Myasthenic Syndromes. In: Pagon RA, Adam MP, Ardinger HH, Wallace SE, Amemiya A, Bean LJH, Bird TD, Ledbetter N, Mefford HC, Smith RJH, Stephens K, editors. GeneReviews® [Internet]. Seattle (WA): University of Washington, Seattle; 1993-2016. May 9, 2003 [updated Jul. 14, 2016].
Cho J-R, Duong AV, Nguyen LTT, Chi S-C. "Design of transdermal matrix patch containing ondansetron". J Pharm Investigation. 2016 46(7): 677-684.
Drachman DB. Myasthenia Gravis. Semin Neurol. 2016; 36:419-424. Epub Sep. 23, 2016.
Engel AG. Congenital Myasthenic Syndromes in 2012. Curr. Neurol Neurosci Rep, 2012; 12(1):92-101.
Gotterer L, Li Y. Maintenance immunosuppression in myasthenia gravis. J Neurol Sci. 2016; 369:294-302. Epub Aug. 28, 2016.
Howard J.F. Clinical Overview of MG. Myasthenia Gravis Foundation of America; 2015.
Koland M et al. 2010: Koland M, Sandeep VP. Charyulu NR. Fast Dissolving Sublingual Films of Ondansetron Hydrochloride: Effect of Additives on in vitro Drug Release and Mucosal Permeation. J Young Pharmacists. 2010, 2(3):216-222.
O'Grady GL, Verschuuren C, Yuen M, Webster R, Menezes M, Fock JM, Pride N, Best HA, Benavides Damm T, Turner C, Lek M, Engel AG, North KN, Clarke NF, MacArthur DG, Kamsteeg EJ, Cooper ST. Variants in SLC18A3, vesicular acetylcholine transporter, cause congenital myasthenic syndrome. Neurology. 2016; 87:1442-1448. Epub Sep. 2, 2016.
Phillips WD, Vincent A. Pathogenesis of myasthenia gravis: update on disease types, models, and mechanisms. FI000Research 2016, 5(F1000 Faculty Rev): 1513 updated Jun. 27, 2016.
Shelton GD. Myasthenia gravis and congenital myasthenic syndromes in dogs and cats: A history and mini-review. Neuromuscul Disord. 2016; 26: 331-334. Epub Mar. 10, 2016.
Smith SV, Lee AG. Update on Ocular Myasthenia Gravis. Neurol Clin. 2017; 35:115-123.

(Continued)

*Primary Examiner* — Doan T Phan
(74) *Attorney, Agent, or Firm* — Transformative Legal, LLC; Len S. Smith; Julie Kurzrok

(57) ABSTRACT

The present invention describes the use of a NK1-antagonist, in constant combination with pyridostigmine, to facilitate the treatment of a patient suffering from myasthenia gravis by providing a therapeutically effective pyridostigmine bromide daily dose without the dose-limiting gastrointestinal adverse effects.

8 Claims, No Drawings

(56) References Cited

OTHER PUBLICATIONS

Myasthenia Gravis Fact Sheet; National Institute of neurological Discorders and Stroke, 2017.
Lexell, "Evidence for Nervous System Degeneration with Advancing Age", Lund University Hospital, 1997 American Society for Nutritional Sciences, pp. 1011S-1013S.
Makarious et al., "Myasthenia gravis: An Emerging Toxicity of Immune Checkpoint Inhibitors", European Journal of Cancer 82(2017) 128-136, Jun. 27, 2017.
Gold et al. Therapeutic Advances in Neurological Disorders, 2008; 1 (2):99-114.

* cited by examiner

PHARMACEUTICAL COMPOSITIONS AND METHODS UTILIZING NEOSTIGMINE AND AN NK-1 ANTAGONIST FOR TREATING MYASTHENIA GRAVIS

RELATED APPLICATIONS

This application is a continuation of PCTUS2018/043636 (published as WO2019-023318), filed Jul. 25, 2018, and claims the benefit of U.S. Provisional Patent Application Ser. No. 62/536,595, filed on Jul. 25, 2017, and of U.S. Provisional Patent Application Ser. No. 62/695,462, filed on Jul. 9, 2018, the disclosures of which are incorporated herein in their entirety by reference.

FIELD OF THE INVENTION

This invention pertains to the field of the treatment of myasthenia gravis and other myasthenic syndromes in patients suffering from this disease. The invention describes new compositions, methods, and combinations for safely treating myasthenia gravis.

OBJECTS OF THE INVENTION

The present invention provides new compositions, methods, and combinations to enable the safe administration of pyridostigmine to mammalian subjects with myasthenic syndromes, including myasthenia gravis, which comprise administering to a patient in need of said treatment an effective daily dose of a NK1-antagonist in combination with an effective daily dose of a pharmaceutically acceptable salt of pyridostigmine.

Definitions

"MG": Myasthenia Gravis. MG is a chronic neuromuscular autoimmune disease, characterized by muscle weakness. The basic abnormality in MG is a reduction in the acetylcholine nicotinic receptors (AChRs) at neuromuscular junctions due to the effects of autoantibodies. About 85% of patients with generalized MG have antibodies to AChRs. Antibodies to other proteins at the neuromuscular junction are present in some cases of MG, such as antibodies to muscle-specific kinase, or to low density lipo-protein 4, or to agrin.

"Myasthenic syndrome": refers to conditions associated with muscle weakness in which the cholinergic transmission at the neuromuscular junction is decreased either because of a decrease in the number and/or dysfunction of post-synaptic nicotinic receptors or to a decrease in the amount of acetylcholine ("Ach") available at the neuromuscular junction due to gene mutations in the presynaptic proteins involved in the synthesis, storage and release of ACh, or to degeneration of cholinergic nerves that innervate muscles. An emerging myasthenic syndrome (with or without auto antibodies to nicotinic receptors) has been reported in association with immune-therapies used for the treatment of certain malignancies. Myasthenic syndromes are sometimes loosely referred to as MG in the medical literature but herein, all MG-like conditions which do not involve autoantibodies to nicotinic receptors will be referred to as myasthenic syndromes. MG itself is a myasthenic syndrome and is considered as such herein, although, as the most prominent myasthenic syndrome it is often mentioned specifically (as in the phrase "MG and other myasthenic syndromes").

"NK1-antagonist": an antagonist of the neurokinin receptor subtype-1, in the literature also referred to as NK1 receptor antagonist or NK1 receptor inhibitor.

"Effective daily dose of NK1-antagonist" this expression, as used herein, refers to a single dose of said NK1-antagonist that is at least as high as the dose preventing or treating nausea and vomiting in a mammalian subject. Said single dose is from 1 µg to 600 mg, normally from 0.01 mg/kg to 1.8 mg/kg of body weight. Alternatively, "Effective daily dose of NK1-antagonist" refers to a daily dose of said NK1-antagonist that is at least as high as the dose preventing or treating nausea and vomiting in pediatric or adult human patients undergoing cancer chemotherapy, said effective daily dose being from 0.03 mg/kg to 3.6 mg/kg of body weight.

"Pyridostigmine": unless otherwise specified, this term, as used herein, refers to a pharmaceutically acceptable salt of pyridostigmine ("pyridostigmine pharmaceutically acceptable salt"), the daily doses and the amounts per unit form thereof being expressed as equivalents of pyridostigmine bromide.

"Effective daily dose of pyridostigmine": this expression, as used herein, refers to a pyridostigmine daily dose, including doses used in the titration period, equivalent to at least 0.5 mg/kg of body weight of pyridostigmine bromide.

"Maximally effective (daily) dose" or "Maximal effective (daily) dose", as used herein for pyridostigmine, refers to any pyridostigmine daily dose allowing the expression of significantly increased or greater pyridostigmine efficacy, heretofore hindered by the typical gastro-intestinal pyridostigmine adverse effects.

"Effective amount per unit form", referring to pyridostigmine, is a pyridostigmine amount per unit form equivalent to at least 0.5 mg of pyridostigmine bromide.

"Mammal" or "mammalian subject" as used herein refers to any class of warm blooded higher vertebrates (such as placentals, marsupials, or monotremes) that nourish their young with milk secreted by mammary glands, have the skin usually more or less covered with hair; and include, but are not limited to, a human, a dog, and a cat.

BACKGROUND OF THE INVENTION

Myasthenia gravis (MG) is a chronic autoimmune disease of the neuromuscular junction (NMJ) caused by antibodies that attack components of the postsynaptic membrane, impair neuromuscular transmission, and lead to varying degrees of weakness and fatigue of skeletal muscle. The prevalence of MG in the United States is estimated at 14 to 20 per 100,000 population, with approximately 36,000 to 60,000 cases in the United States (Howard, 2015). However, MG remains underdiagnosed and the prevalence is probably higher. The disease has also been described in dogs, and cats (Shelton, 2016).

The hallmark of the disease is muscle weakness that increases during periods of activity and improves after periods of rest. Muscular weakness can be generalized or localized to certain muscle groups, and involvement of the bulbar and respiratory muscles can be life threatening (Phillips and Vincent, 2016). Groups of muscles are often involved in typical patterns. Certain muscles such as those that control eye and eyelid movement, facial expression, chewing, talking, and swallowing are often, but not always, involved in the disorder. The muscles that control breathing and neck and limb movements may also be affected.

MG occurs in all ethnic groups and both genders. It most commonly affects young adult women (under 40) and older men (over 60), but it can occur at any age (Myasthenia Gravis Fact Sheet; National Institute of neurological Disorders and Stroke, 2016). In neonatal myasthenia, the fetus may acquire immune proteins (antibodies) from a mother affected with myasthenia gravis. Generally, cases of neonatal MG are temporary, and the child's symptoms usually disappear within 2-3 months after birth (Myasthenia Gravis Fact Sheet; National Institute of neurological Disorders and Stroke, 2016). Other children develop MG indistinguishable from adults. MG in juveniles is uncommon (Myasthenia Gravis Fact Sheet; National Institute of neurological Disorders and Stroke, 2016).

The basic abnormality in MG is a reduction in acetylcholine receptors (AChRs) at neuromuscular junctions due to the effects of autoantibodies that are directed against the AChRs in most patients, or against neighboring proteins involved in the clustering of AChRs, such as MuSK, LRP-4, or agrin (Drachman, 2016).

The diagnosis may be missed during the early stages of the disease, and depends on the recognition of clinical manifestations, the measurement of autoantibodies, and/or electrophysiological features (Drachman, 2016).

Rarely, children may show signs of congenital myasthenia or congenital myasthenic syndrome (CMS). These are not autoimmune disorders, but rather are caused by defective genes that produce abnormal proteins instead of those that normally are involved in cholinergic transmission: acetylcholinesterase (the enzyme that breaks down acetylcholine), acetylcholine receptors, and other proteins present along the muscle membrane (Engel, 2012).

In some rare cases, a myasthenic syndrome is due to bi-allelic variants in the gene encoding the vesicular acetylcholine transporter (VAChT) located in the presynaptic terminal (O'Grady et al, 2016). In other cases, degeneration of the nerves that innervate muscles such as occurs with aging (Lexell, 1997) leads to a myasthenic syndrome. Recently (Makarious et al, 2017), have reported on a myasthenic syndrome involving an emerging toxicity of checkpoint inhibitors used for the treatment of certain malignancies. Most individuals with CMS, or with an immune-oncology therapy-related myasthenic syndrome, or with progressive age-related degeneration of the motor neurons that innervate muscles, benefit from the same treatment as those that are effective in patients with autoimmune MG, namely choline esterase (ChE) inhibitors (Engel 2012; Abicht et al, 2003 updated in 2014).

Ocular myasthenia gravis (OMG) is a localized form of myasthenia gravis in which autoantibodies directed against acetylcholine receptors block or destroy these receptors at the postsynaptic neuromuscular junction. The hallmark of OMG is a history of painless weakness or fatigability of the extraocular muscles and ptosis with normal pupillary function and visual acuity. Clinical, laboratory, electrophysiologic, and pharmacologic tests are available for diagnosis. Treatment can begin with symptom management; there is no cure (Smith and Lee, 2017).

The treatment of myasthenic syndromes involves treatment of the symptoms through the enhancement of cholinergic transmission at the neuromuscular junction by acetylcholine esterase inhibitors (AChEIs) that do not appreciably cross the Blood-Brain-Barrier (BBB), such as pyridostigmine. Patients with autoimmune-related myasthenic syndromes may also benefit from immunotherapy to slow disease progression. Options for immunosuppression include corticosteroids, azathioprine, mycophenolate mofetil, cyclosporine, tacrolimus, methotrexate, rituximab, cyclophosphamide, intravenous immunoglobulin, plasmapheresis, and thymectomy (Gotterer and Li, 2016).

Pyridostigmine treats the symptoms by retarding the enzymatic hydrolysis of ACh at cholinergic synapses, so that acetylcholine concentrations increase at the neuromuscular junction and the effect of acetylcholine is both increased and prolonged. Cholinesterase inhibitors have been shown to cause considerable improvement in some patients with MG and little to none in others (Howard, 2015). Strength rarely returns to normal, possibly because of dose-limiting adverse events (diarrhea, nausea, vomiting) that preclude the use of maximally effective doses of pyridostigmine.

Pyridostigmine bromide (Mestinon®), which does not appreciably cross the BBB, is commonly used for the treatment of MG. No fixed dosage schedule suits all patients. The need for pyridostigmine varies from day-to-day and during the same day in response to infection, menstruation, emotional stress, and hot weather. Adverse effects of pyridostigmine typically consist of gastrointestinal complaints, queasiness, loose stools, nausea, vomiting, abdominal cramps, and diarrhea (Howard, 2015). Increased bronchial and oral secretions are a serious problem in patients with swallowing or respiratory insufficiency. Central nervous system side effects are rare with pyridostigmine.

Gastro-intestinal side effects are an important source of discomfort for the patient, may be a source of non-compliance, or may result in the need to decrease the dose of pyridostigmine to mitigate these side effects whereupon these side effects become dose-limiting. As a consequence, efficacy is reduced.

The literature does not disclose how to safely treat MG with pyridostigmine by increasing the pyridostigmine doses without the undesired gastro-intestinal dose-limiting adverse effects that are inevitably associated with said treatment, thus creating the possibility of an improvement of the condition of patients suffering from this disabling disease.

Thus, the problem of providing tolerable, safe, and maximally effective chronic treatment of MG with pyridostigmine at high, maximally effective doses remains unsolved.

SUMMARY OF THE INVENTION

It has now been found that, by using a neurokinin-1 receptor antagonist, also referred to as NK1 receptor inhibitor or simply NK1-antagonist, in constant combination with pyridostigmine, it is possible to treat mammalian subjects, and particularly humans, dogs, and cats, suffering from symptoms of muscle weakness associated with MG or another myasthenic syndrome by maintaining a therapeutically effective pyridostigmine bromide daily dose without any adverse effect.

In particular, the constant combination of a NK1-antagonist with pyridostigmine enables for the first time the full efficacy of pyridostigmine in the treatment of symptoms of muscle weakness associated with MG and other myasthenic syndromes.

Thus, the present invention provides a method for treating symptoms of muscle weakness associated with MG and other myasthenic syndromes, which comprises administering to a to a mammalian subject in need of said treatment a combination of a NK1-antagonist with an effective dose of pyridostigmine.

Any of the NK1-antagonists disclosed in the literature may be used, in the present invention, in combination with a dose of pyridostigmine that is generally at least as high as that of the pyridostigmine bromide currently used doses for treating MG, and even much higher. The chronic use of this combination mitigates or even eliminates the gastro-intestinal dose-limiting adverse effects of pyridostigmine, thus enabling the safe administration of the recommended or even higher than currently recommended dose of pyridostigmine bromide (maximally effective dose), leading to increased or greater efficacy and safety of pyridostigmine.

According to the present invention, preferably, the NK1-antagonists used are those shown to be effective or approved for treating nausea and vomiting following cancer chemotherapy. In fact, surprisingly, NK1-antagonists, known to block nausea, vomiting, and diarrhea induced by chemotherapeutic drugs, have been shown, in particular when administered at high doses, to also block the gastro-intestinal side effects of pyridostigmine without affecting its efficacy in treating symptoms of muscle weakness associated with MG or other myasthenic syndromes, thus allowing the administration of pyridostigmine maximally effective doses.

This finding is surprising also because, notwithstanding the gravity of the illness and the fact that both pyridostigmine and the NK1-antagonists were two families of products in use during more than a decade, each in its own indication, to date nobody thought that, by combining an effective dose of NK1-antagonist with an effective dose of pyridostigmine, it would have been possible to safely improve the conditions of patients suffering from MG and other myasthenic syndromes.

Thus, the present invention provides a method for treating symptoms of muscle weakness associated with MG and other myasthenic syndromes, which comprises administering to mammalian subjects, and in particular, humans, dogs, and cats, in need of said treatment an effective daily dose of a NK1-antagonist in combination with an effective daily dose of a pharmaceutically acceptable salt of pyridostigmine.

According to an embodiment, the invention provides a pharmaceutical combination comprising a NK1-antagonist, at a daily dose that is at least as high as the pediatric or adult dose shown to be effective for the prevention or treatment of chemotherapy-induced nausea and vomiting, and a maximally effective dose of a pyridostigmine pharmaceutically acceptable salt.

According to another embodiment, the invention provides a NK1-antagonist, in a pharmaceutical composition comprising, as an active ingredient, said NK1-antagonist in an amount at least as high as the pediatric or adult dose shown to be effective for the prevention or treatment of chemotherapy-induced nausea and vomiting, in admixture with a pharmaceutical carrier, for use for preventing or attenuating the dose-limiting gastrointestinal adverse effects of pyridostigmine in the treatment of symptoms of muscle weakness associated with MG and other myasthenic syndromes in a mammalian subject in need of said treatment.

According to a further embodiment, the invention includes the use of a NK1-antagonist for the preparation of a medicament including a pharmaceutical composition comprising, as an active ingredient, said NK1-antagonist, in an amount per unit form at least as high as the pediatric or adult dose shown to be effective for the prevention or treatment of chemotherapy-induced nausea and vomiting (effective amount per unit form), in admixture with a pharmaceutical carrier, for attenuating or even abrogating the gastro-intestinal adverse effects of pyridostigmine in the treatment of symptoms of muscle weakness associated with MG and other myasthenic syndromes in a mammalian subject in need of said treatment.

As set forth above, the amount per unit form of the NK1-antagonist is at least as high as the pediatric or adult dose shown to be effective for the prevention or treatment of chemotherapy-induced nausea and vomiting and may be up to 4 times said dose and even up to 6 times said dose.

Said composition comprising said NK1-antagonist for the first time allows the safe administration of currently used effective doses and also higher, maximally effective pyridostigmine doses to mammalian subjects suffering from symptoms of muscle weakness associated with MG or other myasthenic syndromes, with the consequent expression of the pyridostigmine increased or greater efficacy.

According to yet a further embodiment, the invention provides a pharmaceutical fixed-dose combination including a pharmaceutical composition in dosage unit form comprising a NK1-antagonist, in an amount per unit form that is at least as high as the pediatric or adult dose shown to be effective for the prevention and treatment of chemotherapy-induced nausea and vomiting, as Component (a) and an effective amount per unit form of a pyridostigmine pharmaceutically acceptable salt, as Component (b), in admixture with a pharmaceutical carrier or vehicle.

According to a preferred embodiment, the invention provides a pharmaceutical combination comprising an approved NK1-antagonist, at a dose that is at least as high as the pediatric or adult dose approved for the prevention or treatment of chemotherapy-induced nausea and vomiting, and an effective, especially maximally effective, dose of a pyridostigmine pharmaceutically acceptable salt.

According to an aspect of this preferred embodiment, the invention provides an approved NK1-antagonist, in a pharmaceutical composition comprising, as an active ingredient, said NK1-antagonist in an amount at least as high as the pediatric or adult dose approved for the prevention or treatment of chemotherapy-induced nausea and vomiting, in admixture with a pharmaceutical carrier, for use for preventing, attenuating or even abrogating the gastrointestinal adverse effects of pyridostigmine in the treatment of myasthenia gravis and other myasthenic syndromes.

According to a further aspect of this preferred embodiment, the invention includes the use of an approved NK1-antagonist for the preparation of a medicament consisting of a pharmaceutical composition comprising, as an active ingredient, said NK1-antagonist, in an amount at least as high as the pediatric or adult dose approved for the prevention or treatment of chemotherapy-induced nausea and vomiting, in admixture with a pharmaceutical carrier, for preventing, attenuating or even abrogating the gastrointestinal adverse effects of pyridostigmine in the treatment of myasthenia gravis and other myasthenic syndromes.

According to yet a further aspect of this preferred embodiment, the invention provides a pharmaceutical fixed-dose combination comprising a pharmaceutical composition comprising a NK1-antagonist, in an amount per unit form that is at least as high as the pediatric or adult dose approved for the prevention and treatment of chemotherapy-induced nausea and vomiting, as Component (a) and an effective amount per unit form of a pyridostigmine pharmaceutically acceptable salt, as Component (b), in admixture with a pharmaceutical carrier or vehicle.

As set forth above, the amount of the NK1-antagonist is at least as high as the pediatric or adult dose approved for the prevention or treatment of chemotherapy-induced nausea and vomiting and may be up to 6 times said dose.

Among the approved NK1-antagonists to be used in combination, including fixed-dose combinations, with pyridostigmine, aprepitant and pharmaceutically acceptable salts and solvates and prodrugs thereof, rolapitant and pharmaceutically acceptable salts and solvates thereof, and netupitant and pharmaceutically acceptable salts and solvates and prodrugs thereof are particularly advantageous.

In the above combination, including fixed-dose combinations, said amount per unit form of said NK1-antagonist administered orally Component (a) in said composition normally is from 1 μg to 600 mg. The NK1-antagonist daily dose is from 1 μg to 600 mg.

In the above combination, including fixed-dose combinations, the amount of pyridostigmine in an Immediate Release ("IR") unit form (amount per unit form) will range from 15 mg to 800 mg, normally from 30 mg to 800 mg, from 30 mg to 500 mg, from 30 mg to 400 mg, from 30 mg to 200 mg, from 30 mg to 180 mg, from 30 mg to 120 mg or from 30 mg to 90 mg, depending on safety and tolerability (per day the dose is from 180 mg to 2400 mg, and even more, normally from 180 mg to 1200 mg, from 180 mg to 1080 mg or from 180 mg to 720 mg).

The dose of pyridostigmine in Extended Release ("ER") unit form will range from 90 mg to 800 mg, normally from 90 mg to 400 mg, from 90 mg to 360 mg or from 90 to 240 mg, to be administered 3-6 times per day.

When the NK1-antagonist is aprepitant or a pharmaceutically acceptable salt thereof, its dose per IR unit form, in combination with pyridostigmine, will correspond to from 10 mg to 125 mg of aprepitant.

When the NK1-antagonist is rolapitant, the dose/unit form in combination with IR-pyridostigmine at the above doses/unit form, will range from 15 mg to 270 mg in an IR formulation. The present invention further provides a kit or package comprising a pharmaceutical combination or pharmaceutical or veterinary composition as described herein, and instructions for use of the same for treatment of a MG and other myasthenic syndromes in a patient in need thereof.

DETAILED DESCRIPTION

The present invention provides, according to certain aspects,
- a method for safely improving the conditions or symptoms of muscle weakness of mammalian subjects, particularly, humans, dogs, and cats, suffering from MG or other myasthenic syndromes by treating said subjects with a NK1-antagonist in combination with pyridostigmine;
- a NK1-antagonist, for use in the treatment of MG and other myasthenic syndromes in combination with pyridostigmine;
- the use of a NK1-antagonist for the preparation of a medicament for the treatment of symptoms of muscle weakness associated with MG and other myasthenic syndromes in combination with pyridostigmine; and
- a fixed-dose combination consisting of a pharmaceutical composition in dosage unit form comprising, as active ingredients, a NK1-antagonist Component (a) and pyridostigmine Component (b).

The present invention also relates to the use of a NK1-antagonist for the preparation of a medicament for the treatment of symptoms of muscle weakness associated with MG and other myasthenic syndromes, said medicament being a pharmaceutical composition in dosage unit form comprising, as an active ingredient, said NK1-antagonist Component (a), and, as a second active ingredient, said pyridostigmine Component (b), in admixture with a pharmaceutically acceptable carrier or vehicle.

The NK1-Antagonist Component (a)

Any NK1-antagonist may be used for providing the safe treatment of MG and other myasthenic syndromes with normal, but also with high and very high, maximally effective pyridostigmine doses. Antagonists of the NK1 receptor that are shown to be effective for the prevention or treatment of chemotherapy-induced nausea and vomiting are particularly useful according to the present invention.

The NK1-antagonist is preferably selected from the group consisting of
- 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one (aprepitant); described in U.S. Pat. No. 5,719,147, and in a liquid oral formulation, in US 2017/0035774, and in an injectable emulsion in a single-dose vial for intravenous use containing 130 mg aprepitant in 18 ml of emulsion (Cinvanti®), described in U.S. Pat. No. 9,808,465 (the contents of each disclosure is incorporated herein in its entirety by reference);
- [3-{[(2R,3S)-2-[(1R)-1-[3,5-bis(trifluoromethyl)phenyl]ethoxy]-3-(4-fluorophenyl)morpholin-4-yl]methyl}-5-oxo-2H-1,2,4-triazol-1 yl]phosphonic acid (fosaprepitant), disclosed, for example as dimeglumine salt in U.S. Pat. No. 5,691,336 and as di(cyclohexylamine) salt in US 2016/355533 (the contents of each disclosure is incorporated herein in its entirety by reference);
- (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide (casopitant) described in U.S. Pat. No. 7,294,630 (the contents of each disclosure is incorporated herein in its entirety by reference);
- (2S)-1-[(3aS,4S,7aS)-4-hydroxy-4-(2-methoxyphenyl)-7,7-diphenyl-1,3,3a,5,6,7a-hexahydroisoindol-2-yl]-2-(2-methoxyphenyl)propan-1-one (INN: dapitant);
- (2S,3S)—N-(5-tert-Butyl-2-methoxybenzyl)-2-(diphenylmethyl)-1-azabicyclo[2.2.2]octan-3-amine (maropitant), disclosed in U.S. Pat. No. 5,807,867, WO2005/082416 and EP 3173071 (the contents of each disclosure is incorporated herein in its entirety by reference);
- (2S,3S)-2-Diphenylmethyl-3-[(5-isopropyl-2-methoxybenzyl)amino]quinuclidine (ezlopitant), disclosed by Evangelista S (2001). "Ezlopitant. Pfizer"; Current Opinion in Investigational Drugs: 2 (10): 1441-3; reviewed in Drugs: the Investigational Drugs Journal 6 (8): 758-72 (the content of each disclosure is incorporated herein in its entirety by reference);
- (2S)—N-{2-[3,5-bis(trifluoromethyl)phenyl]ethyl}-2-[4-(cyclopropylmethyl)piperazin-1-yl]-N-methyl-2-phenylacetamide (INN figopitant);
- N-[(2R)-1-[Acetyl-[(2-methoxyphenyl)methyl]amino]-3-(1H-indol-3-yl)propan-2-yl]-2-(4-piperidin-1-ylpiperidin-1 yl)acetamide (lanepitant);
- 2-[3,5-bis(trifluoromethyl)phenyl]-N,2-dimethyl-N-[4-(2-methylphenyl)-6-(4-methyl-1-piperazinyl)-3-pyridinyl]propanamide (netupitant) described in U.S. Pat. Nos. 6,297,375, 6,719,996 and 6,593,472, and, in an oral composition, comprising 300 mg of netupitant and palonosetron hydrochloride in an amount equivalent to 0.5 mg of palonosetron base, herein below referred to as "netupitant-300/palonosetron-0.5", described in U.S. Pat. No. 8,951,969 (the content of each disclosure is incorporated herein in its entirety by reference);
- {4-[5-{2-[3,5-bis(trifluoromethyl)phenyl]-N,2-dimethyl-propanamido}-4-(2-methylphenyl)pyridin-2-yl]-1-methylpiperazin-1-ium-1-yl}methyl hydrogen phosphate (INN: fosnetupitant), described in WO 2013/082102 and, in a pure crystalline form, in US 2017/0096442, available in an injectable composition, comprising 235 mg of fosnetupitant and palonosetron hydrochloride in an amount equivalent to 0.25 mg of palonosetron base (Akynzeo® for injection), herein below referred to as "netupitant-235/palonosetron-0.25" (the content of each disclosure is incorporated herein in its entirety by reference);

(2R,4S)-4-[(8aS)-6-oxo-1,3,4,7,8,8a-hexahydropyrrolo[1,2-a]pyrazin-2-yl]-N-[(1R)-1-[3,5-bis(trifluoromethyl)phenyl]ethyl]-2-(4-fluoro-2-methylphenyl)-N-methylpiperidine-1-carboxamide (orvepitant);

(5S,8S)-8-({(1R)-1-[3,5-bis(trifluoromethyl)phenyl]ethoxy}methyl)-8-phenyl-1,7-diazaspiro[4.5]decan-2-one (rolapitant), described in U.S. Pat. No. 7,049,320 and, for an injectable form thereof, in U.S. Pat. No. 9,101,615 (the content of each disclosure is incorporated herein in its entirety by reference);

3-((3aR,4R,5S,7aS)-5-[(1R)-1-[3,5-bis(trifluoromethylphenyl)ethoxy]-4-(4-fluorophenyl)-1,3,3a,4,5,6,7,7a-octahydroisoindol-2-ylcyclopent-2-en-1-one (serlopitant) described in U.S. Pat. Nos. 7,544,815 and 7,217,731 (the content of each disclosure is incorporated herein in its entirety by reference);

2-(S)-(4-Fluoro-2-methyl-phenyl)-piperazine-1-carboxylic acid [1-(R)-(3,5-bis-trifluoromethyl-phenyl)-ethyl]-methyl-amide (vestipitant), described in WO 2001/25219 and, in intravenous formulation having a reduced tendency to cause hemolysis, in WO 2012/175434 (the content of each disclosure is incorporated herein in its entirety by reference); and (2S,3S)—N-[(2-methoxy-5-[5-(trifluoromethyl)tetrazol-1-yl]phenylmethyl]-2-phenylpiperidin-3-amine (GR2015171, vofopitant), described in U.S. Pat. No. 5,703,240 (see also U.S. Pat. No. 8,093,268) and also disclosed by Gardner C J et al. RegulPept. 1996 Aug. 27; 65(1):45-53 (the content of each disclosure is incorporated herein in its entirety by reference).

Preferably, said NK1-antagonist is selected from the group consisting of aprepitant and pharmaceutically acceptable salts, solvates and prodrugs thereof.

Illustrative examples of pharmaceutically acceptable salts of basic advantageous NK1-antagonists include acid addition salts with mineral or organic acids such as hydrochloric acid, hydrobromic acid, hydriodic acid, sulfuric acid, sulfamic acid, nitric acid, carbonic acid, phosphoric acid, formic acid, acetic acid, propionic acid, stearic acid, glycolic acid, oxalic acid, malonic acid, succinic acid, fumaric acid, maleic acid, hydroxymaleic acid, lactic acid, malic acid, tartaric acid, citric acid, ascorbic acid, phenylacetic acid, benzoic acid, salicylic acid, 2-acetoxybenzoic acid, methanesulfonic acid, ethanesulfonic acid, 2-hydroxyethanesulfonic (isethionic) acid, p-toluenesulfonic acid, 2-naphthalenesulfonic acid, 4-amino-benzenesulfonic (sulfanilic) acid, 2,6-naphthalenedisulfonic acid, 1,5-naphthalenedisulfonic acid, aspartic acid, glutamic acid, and pamoic (embonic) acid. Said salt may be solvated with a solvent, said solvent normally being water.

Illustrative examples of pharmaceutically acceptable salts of acidic NK1-antagonists such as fosaprepitant include salts with inorganic bases such as alkaline metal or alkaline-earth metal salts, and salts with organic bases such as dicyclohexylamine salts, N-methyl-D-glucamine (meglumine) salts, and salts with amino acids, as described in U.S. Pat. No. 5,691,336, the contents of which are incorporated herein in their entirety by reference.

Aprepitant, fosaprepitant meglumine, fosaprepitant di(cyclohexylamine), rolapitant, rolapitant hydrochloride, netupitant-300/palonosetron-0.5, and fosnetupitant-235/palonosetron-0.25 are particularly advantageous NK1-antagonists.

Fosaprepitant, fosaprepitant meglumine, fosaprepitant di(cyclohexyl amine), are prodrugs of aprepitant, and fosnetupitant is a prodrug of netupitant. Thus, the expressions "fosaprepitant and pharmaceutically acceptable salts and solvates and prodrugs thereof and "netupitant and pharmaceutically acceptable salts and solvates and prodrugs thereof include aprepitant, fosaprepitant, fosaprepitant meglumine, fosaprepitant di(cyclohexylamine), and, respectively, netupitant and fosnetupitant.

Antagonists of the NK1 receptor that are approved for the prevention or treatment of postoperative nausea and vomiting or for the prevention of chemotherapy-induced nausea and vomiting are particularly useful according to the present invention. In particular, aprepitant is commercially available (Emend®) in capsules containing 40 mg, 80 mg, or 125 mg aprepitant, in one 150-mg powder in single-dose glass vial, for reconstitution for intravenous injection, or, as fosaprepitant dimeglumine (Emend® Injection), in vials containing 115 mg or 150 mg fosaprepitant; rolapitant is available (Varubi®) in 90-mg tablets; and netupitant-300/palonostron-0.5, available (Akynzeo®) in a fixed-dose combination in capsules containing 300 mg of netupitant and 0.5 mg of the NK1-antagonist palonosetron (as hydrochloride); and fosnetupitant-235/palonosetron-0.25 mg, available (Akynzeo® for injection) in single-dose vial for reconstitution for intravenous injection, are particularly advantageous NK1-antagonists.

Aprepitant and pharmaceutically acceptable salts and solvates and prodrugs thereof; rolapitant and pharmaceutically acceptable salts and solvates and prodrugs thereof; and netupitant and pharmaceutically acceptable salts and solvates and prodrugs thereof are particularly advantageous NK1-antagonists in the combination of the present invention.

More particularly, in said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; netupitant-300/palonosetron-0.5 once a day; and fosnetupitant-235/palonosetron-0.25 once a day.

For its administration to a patient suffering from MG or a myasthenic syndrome, in combination with pyridostigmine, each of the above NK1-antagonists is formulated in a pharmaceutical composition in dosage unit form comprising, as an active ingredient, said NK1-antagonist, in admixture with a pharmaceutical carrier or vehicle.

In particular, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg of netupitant; fosnetupitant and pharmaceutically acceptable salts and solvates thereof; netupitant-300/palonosetron-0.5; and fosnetupitant-235/palonosetron-0.25.

Advantageously, said NK1-antagonist is aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg.

As set forth above, by using a NK1-antagonist in combination with pyridostigmine, it is possible to treat a patient suffering from MG or a myasthenic syndrome by maintaining a therapeutically effective pyridostigmine daily dose with minimal adverse effect.

Thus, in order to assure a sure, safe and concurrent administration of said NK1-antagonist and pyridostigmine, the present invention provides a fixed-dose combination consisting of a pharmaceutical composition in dosage unit form comprising an effective amount per unit form of said NK1-antagonist and an effective amount per unit form of said pyridostigmine, in admixture with a pharmaceutical carrier or vehicle.

These NK1-antagonist/pyridostigmine fixed-dose combinations are illustrated in the "Fourth aspect of the invention" section below.

The Pyridostigmine Component (b)

Pyridostigmine bromide is currently used for the oral treatment of patients suffering from MG, in particular in 60 mg tablets for IR administration, in 60 mg per 5 ml syrup, and in ER-unit forms containing 90 mg of pyridostigmine bromide.

According to the FDA approved label for pyridostigmine, in order to have a more complete response to the pyridostigmine treatment, high pyridostigmine doses should be administered, up to 1500 mg/day, using the 60 mg IR-tablets, or up to 1080 mg/day, using the 180 mg ER-tablets, possibly accompanied by supplemental IR-tablets. However, as set forth above, said doses are not tolerated in most patients. Higher doses than the currently recommended doses might provide further improvement and even a near-to-complete response, i.e., the complete alleviation of symptoms.

According to the present invention, by constantly combining (by concurrent administration) pyridostigmine bromide with a NK1-antagonist, said treatment becomes safe, and very high, maximally effective doses are attained without appreciable adverse effects, thus improving the patients' conditions.

In addition, the present invention also allows the treatment of other mammals, in particular cats and dogs.

Normally, according to the present invention pyridostigmine is administered at a single dose calculated on the body weight of such mammals and administered, in combination with a NK1-antagonist, to said mammals in an unit form comprising or delivering said pyridostigmine in predetermined amount.

In particular, pyridostigmine is administered to such mammals at a single dose, including titration doses, equivalent to from 0.05 mg/kg to 6 mg/kg of body weight of pyridostigmine bromide, in a unit form comprising or delivering a pyridostigmine amount equivalent to from 0.4 mg to 800 mg of pyridostigmine bromide.

For example, pyridostigmine is administered to a mammal at a single oral dose equivalent to from 0.5 mg/kg to 6 mg/kg of body weight of pyridostigmine bromide, given in unit forms comprising or delivering a pyridostigmine amount per unit form equivalent to from 2 mg to 800 mg of pyridostigmine bromide, said unit form being administered from 3-times/day to 6-times/day.

Pyridostigmine may also be administered to such mammals at a single dose equivalent to from 0.1 mg/kg to 1.2 mg/kg of body weight of pyridostigmine bromide, given in unit form for subcutaneous administration, comprising an amount per unit form equivalent to from 0.4 mg to 200 mg of pyridostigmine bromide, said unit form being administered once or twice per day.

In combination with a NK1-antagonist, the effective pyridostigmine daily dose-range for the treatment of a myasthenic syndrome in a mammal, including parenteral (intravenous, intravenous infusion, subcutaneous, subcutaneous infusion, transcutaneous or intramuscular), oral and other administration ways' doses as illustrated in "The formulations" section below, is equivalent to from 0.4 mg to 2400 mg and even more, of pyridostigmine bromide.

Thus, for example, an effective oral daily dose from 180 mg to 2400 mg (in the severe forms of the disease, from 1650 mg to 2400 mg and even more) normally from 180 mg to 1200 mg, in pyridostigmine bromide, may be safely administered, in combination with a NK1-antagonist, to a patient suffering from MG or other myasthenic syndrome.

Appropriate unit forms consisting of a pharmaceutical or veterinary composition comprising a pharmaceutically acceptable salt of pyridostigmine, in an amount per unit form equivalent to from 0.4 mg to 800 mg, from 15 mg to 800 mg, or from 30 mg to 800 mg of pyridostigmine bromide are provided by the present invention. These compositions are safely administered for the treatment MG or other myasthenic syndromes, constantly and concurrently in combination with a NK1-antagonist.

A safer administration is assured by combining, in the same unit form, a NK1-antagonist, in an amount per unit form of from 1 μg to 600 mg; and pyridostigmine, in an amount per unit form equivalent to from 0.4 mg to 800 mg, normally from 15 mg to 800 mg of pyridostigmine bromide.

Preferably, said NK1-antagonist is one of the approved NK1-antagonists described in "The NK1-antagonist" section, in an amount per unit form as described in the same section and said pyridostigmine is pyridostigmine bromide.

First Aspects of the Invention

According to a first aspect, the present invention provides a method for safely improving the conditions of a mammal, in particular a human being or another mammal such as a cat or a dog, suffering from symptoms of muscle weakness associated with MG or another myasthenic syndrome, by chronically administering to said mammal a NK1-antagonist in constant combination with pyridostigmine.

Any of the NK1-antagonists illustrated in "The NK1-antagonist" section above may be used for improving the conditions of a mammalian subject suffering from a myasthenic syndrome, in combination with pyridostigmine at the currently used doses and, in particular, at heretofore intolerable doses and even at very high doses, as illustrated in "The pyridostigmine Component (b)" section above.

In particular, the present invention describes a method for safely improving the conditions or symptoms of muscle weakness of patients suffering from MG or another myasthenic syndrome, and treated with pyridostigmine by chronically administering to said patients a NK1-antagonist. More particularly, the present invention provides a method for treating symptoms of muscle weakness associated with MG and other myasthenic syndromes, which comprises administering to a patient in need of said treatment an effective daily dose of a NK1-antagonist in combination with an effective daily dose of pyridostigmine.

In carrying out the method of the present invention, the daily dose of these NK1-antagonists is at least as high as that preventing or treating nausea and vomiting in pediatric or adult patients under cancer chemotherapy according to the current protocols for said treatment.

The NK1-antagonists allowing safe treatment with pyridostigmine, in particular at heretofore intolerable doses and even at high doses, with their doses per unit form and daily doses to be administered to said mammalian subject, are illustrated in "The NK1-antagonist" section.

According to an embodiment, said NK1-antagonist is selected from the group consisting of aprepitant and pharmaceutically acceptable salts and solvates and prodrugs thereof, fosaprepitant and pharmaceutically acceptable salts and solvates and prodrugs thereof, rolapitant and pharmaceutically acceptable salts and solvates and prodrugs thereof, netupitant and pharmaceutically acceptable salts and solvates and prodrugs thereof, each at a daily dose illustrated in "The NK1-antagonist" section, netupitant-300/palonosetron-0.5, administered once a day; fosnetupitant-235/palonosetron-0.25, administered once a day; and said pyridostigmine is selected from the group consisting of pharmaceutically acceptable salts of pyridostigmine, at a daily dose as illustrated above in "The Pyridostigmine Component (b)" section.

In particular, said daily dose of said NK1-antagonist is from 1 µg to 600 mg normally from 1 mg to 600 mg, or from 1 mg to 300 mg; and said daily dose of said pyridostigmine is equivalent to from 0.4 mg to 2400 mg of pyridostigmine bromide.

Normally, in the treatment of symptoms of muscle weakness associated with MG and other myasthenic disorders in a mammalian subject, and in particular, humans, dogs, and cats, pyridostigmine is administered to said mammalian subject:
  either at a single oral dose equivalent to from 0.5 mg/kg to 6 mg/kg of body weight of pyridostigmine bromide, given in unit forms comprising an amount per unit form equivalent to from 2 mg to 800 mg of pyridostigmine bromide, said unit form being administered from three times per day to six times per day;
  or at a single subcutaneous dose equivalent to from 0.1 mg/kg to 1.2 mg/kg of body weight of pyridostigmine bromide, said subcutaneous dose being in unit forms comprising a pyridostigmine amount equivalent to from 0.4 mg to 200 mg of pyridostigmine bromide, said unit forms being administered from once or twice per day.

Preferably, a human patient suffering from symptoms of muscle weakness associated with MG or other myasthenic disorders is treated, in combination with pyridostigmine, with a NNK1-antagonist selected from the group consisting of aprepitant, at a daily oral or intravenous dose of from 10 mg to 250 mg; fosaprepitant meglumine, at daily injectable dose equivalent to from 10 mg to 250 mg of aprepitant; rolapitant, at a daily oral dose of from 15 mg to 270 mg, or from 30 mg to 270 mg; netupitant-300/palonosetron-0.5 once a day; and fosnetupitant-235/palonosetron-0.25 once a day.

The above daily doses of the above NK1-antagonists allow the safe administration of high pyridostigmine daily doses.

More particularly, the above daily doses of the above NK1-antagonist allow the safe administration of pyridostigmine currently used daily doses, as well as of maximally effective oral doses equivalent to from 1080 mg/day to 2400 mg/day, from 1200 mg/day to 2400 mg/day or from more than 1500 mg/day to 2400 mg/day, and even more, of pyridostigmine bromide; and maximally effective parenteral (intramuscular, subcutaneous or intravenous) daily doses equivalent to from 36 mg/day to 80 mg/day, from 40 mg/day to 80 mg/day or from more than 50 mg/day to 80 mg/day of pyridostigmine bromide, to a human patient suffering from symptoms of muscle weakness associated with MG or other myasthenic syndromes.

For said treatment, said NK1-antagonist is formulated in a pharmaceutical composition in dosage unit form comprising an effective amount per unit form of said NK1-antagonist, normally from 1 µg to 600 mg, in admixture with a pharmaceutical carrier or vehicle. Said composition, is administered to said patient at the above daily doses, in combination with pyridostigmine, also in a pharmaceutical composition comprising or delivering an effective amount per unit form of pyridostigmine, normally equivalent to from 2 mg to 800 mg of pyridostigmine bromide, at the aforementioned daily doses.

Preferably, said NK1-antagonist active ingredient of said pharmaceutical composition is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg; netupitant-300/palonosetron-0.5; and fosnetupitant-235/palonosetron-0.25.

Said NK1-antagonist and said pyridostigmine may also be co-formulated in a pharmaceutical composition, in admixture with a pharmaceutical carrier or vehicle as illustrated in the "Fourth aspect of the invention" below.

The method of the present invention allows a safe treatment of symptoms of muscle weakness associated with MG or other myasthenic disorders in a mammalian subject.

Second Aspect of the Invention

According to a second aspect, the invention provides a NK1-antagonist for use in the treatment of symptoms of muscle weakness associated with MG and other myasthenic syndromes, in combination with pyridostigmine.

Any NK1-antagonist, in particular those that are shown to be effective for the prevention or treatment of chemotherapy-induced nausea and vomiting may be used, in a combination, including fixed-dose combinations, with pyridostigmine according to this aspect of the present invention. Preferably, said NK1-antagonists are those approved for the prevention or treatment of chemotherapy-induced nausea and vomiting.

For said treatment, said NK1-antagonist single dose is formulated in a pharmaceutical or veterinary composition in dosage unit form comprising an effective amount per unit form of said NK1-antagonist, in admixture with a pharmaceutical carrier or vehicle.

In particular, the NK1-antagonist is administered to a mammalian subject in a pharmaceutical or veterinary composition comprising said NK1-antagonist in an effective amount per unit form of from 1 µg to 600 mg to be administered once a day in combination with pyridostigmine, also in a pharmaceutical or veterinary composition in dosage unit form comprising a pyridostigmine amount per unit form equivalent to from 0.4 mg to 800 mg of pyridostigmine bromide, to be administered at a daily dose of from 0.4 mg to 2400 mg.

The amounts per unit form of said NK1-antagonists and the daily doses to be administered to a mammal such as a cat or a dog, or a human patient suffering from symptoms of muscle weakness associated with MG or another myasthenic syndrome in combination with pyridostigmine are described in "The NK1-antagonist" section.

An advantageous NK1-antagonist to be used in combination with 6-propylamino-4,5,6,7-tetrahydro-1,3-benzothiazole-2-amine is selected from the group consisting of aprepitant and pharmaceutically acceptable salts and solvates thereof, fosaprepitant and pharmaceutically acceptable salts and solvates thereof, casopitant and pharmaceutically acceptable salts and solvates thereof, maropitant and pharmaceutically acceptable salts and solvates thereof, ezlopitant and pharmaceutically acceptable salts and solvates thereof, lanepitant and pharmaceutically acceptable salts and solvates thereof, netupitant and pharmaceutically acceptable salts and solvates thereof, fosnetupitant and pharmaceutically acceptable salts and solvates thereof: orvapitant and pharmaceutically acceptable salts and solvates thereof, rolapitant and pharmaceutically acceptable salts and solvates thereof, serlopitant and pharmaceutically acceptable salts and solvates thereof, vestipitant and pharmaceutically acceptable salts and solvates thereof, vofopitant and pharmaceutically acceptable salts and solvates thereof, netupitant-300/palonosetron-0.5; and fosnetupitant-235/palonosetron-0.25.

More particularly, in said combination, said NK1-antagonist is selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; netupitant-300/palonosetron-0.5 once a day; and fosnetupitant-235/palonosetron-0.25 once a day.

Said composition comprising said NK1-antagonist provides for the safe treatment of symptoms of muscle weakness associated with MG and other myasthenic syndromes, in combination with pyridostigmine, administered at a daily dose equivalent to from 0.4 mg to 2400 mg of pyridostigmine bromide.

In said combination, pyridostigmine may be administered to mammalian subjects at a single oral dose equivalent to from 0.5 mg/kg to 6 mg/kg of body weight of pyridostigmine bromide. Said single dose is formulated in a unit form comprising an amount of from 2 mg to 800 mg of pyridostigmine bromide, said unit form being administered from three times per day to six times per day.

Said composition also allows the administration of a single pyridostigmine subcutaneous dose equivalent to from 0.1 mg/kg to 1.2 mg/kg of body weight of pyridostigmine bromide, said subcutaneous dose being in a unit form comprising a pyridostigmine amount equivalent to from 0.4 mg to 200 mg of pyridostigmine bromide, said unit form being administered once or twice per day.

In particular, said composition provides for the safe treatment of a patient suffering from symptoms of muscle weakness associated with MG or other myasthenic syndrome, in combination with pyridostigmine oral daily doses equivalent to from 180 mg to 2400 mg (and even more), normally from 180 mg to 1500 mg, from 180 mg to 1200 mg, from 180 mg to 1080 mg or from 180 mg to 720 mg of pyridostigmine bromide.

More particularly, said composition provides for the administration of pyridostigmine maximally effective oral doses equivalent to from 1080 mg/day to 2400 mg/day, from 1200 mg/day to 2400 mg/day or from more than 1500 to 2400 mg/day, and even more, of pyridostigmine bromide to a human patient suffering from symptoms of muscle weakness associated with MG or other myasthenic syndromes.

Third Aspect of the Invention

According to a third aspect, the invention provides the use of a NK1-antagonist for the preparation of a medicament for the treatment of a mammal such as a cat or a dog, or a human patient suffering from symptoms of muscle weakness associated with MG or other myasthenic syndromes, in combination with pyridostigmine.

Said medicament for the treatment of symptoms of muscle weakness associated with MG and other myasthenic syndromes comprises a NK1-antagonist formulated in a pharmaceutical or veterinary composition wherein said NK1-antagonist is in admixture with a pharmaceutical carrier or vehicle, to be administered, concurrently or sequentially, in combination with pyridostigmine.

In said pharmaceutical or veterinary composition, said NK1-antagonist is in admixture with a pharmaceutical carrier and formulated in unit forms for oral, intravenous, intramuscular, subcutaneous, transcutaneous, or transdermal administration, as described in "The formulations" section below.

According to this third aspect of the present invention, any of the NK1-antagonists described in "The NK1-antagonist Component (a)" section may be used as an active ingredient of the pharmaceutical or veterinary composition indicated as a medicament for the treatment of a mammalian subject suffering from symptoms of muscle weakness associated with MG or other myasthenic syndromes, in combination with pyridostigmine doses as described in "The Pyridostigmine Component (b)" section.

According to an embodiment of this third aspect, said medicament is a pharmaceutical or veterinary composition in dosage unit form comprising, as an active ingredient, said NK1-antagonist, in an amount per unit form of from 1 μg to 600 mg, normally from 1 mg to 600 mg or from 1 mg to 300 mg, in admixture with a pharmaceutical carrier or vehicle.

Said medicament, in the above dose per unit form is destined to be administered to said mammalian subject at a daily dose of from 1 μg to 600 mg, normally from 1 mg to 600 mg or from 1 mg to 300 mg, in combination with pyridostigmine, also in pharmaceutical or veterinary composition in dosage unit form comprising a pyridostigmine amount per unit form equivalent to from 0.4 mg to 800 mg of pyridostigmine bromide, said unit form being administered from three times per day to six times per day.

In particular, said medicament includes a pharmaceutical or veterinary composition comprising a NK1-antagonist active ingredient selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant; rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg; netupitant-300/palonosetron-0.5; and fosnetupitant-235/palonosetron-0.25.

In said combination, said NK1-antagonist is preferably selected from the group consisting of aprepitant and pharmaceutically acceptable salts and solvates thereof, at a daily dose equivalent to from 10 mg to 250 mg of aprepitant; fosaprepitant and pharmaceutically acceptable salts and solvates thereof, at a daily dose equivalent to from 10 mg to 250 mg of aprepitant; rolapitant and pharmaceutically acceptable salts and solvates thereof, at a daily dose equivalent to from 15 mg to 270 mg of rolapitant, netupitant and pharmaceutically acceptable salts and solvates thereof, at a daily dose equivalent to from 300 mg to 600 mg; netupitant-300/palonosetron-0.5 once a day; and fosnetupitant-235/palonosetron-0.25 once a day.

According to this third aspect of the present invention, said medicament comprising said NK1-antagonist is destined to be administered to said mammalian subject, at the above daily dose, in combination with pyridostigmine, administered at a daily dose equivalent to from 0.4 mg to 2400 mg of pyridostigmine bromide.

Advantageously, Said Pyridostigmine is Administered either at a single oral dose equivalent to from 0.5 mg/kg to 6 mg/kg of body weight of pyridostigmine bromide, given in an unit form comprising an amount per unit form equivalent to from 15 mg to 800 mg of pyridostigmine bromide, said unit form being administered from three times per day to six times per day;

or at a single subcutaneous dose equivalent to from 0.1 mg/kg to 1.2 mg/kg of body weight of pyridostigmine bromide, said subcutaneous dose being in a unit form comprising a pyridostigmine amount equivalent to from 0.4 mg to 200 mg of pyridostigmine bromide, said unit form being administered from once or twice per day.

In certain preferred embodiments, the present invention provides pharmaceutical compositions including, as one of their active ingredients, a pharmacologically active amount of a NK1-antagonist as shown above or of one of its pharmaceutically acceptable salts, in mixture with a pharmaceutical carrier or vehicle.

In said combination, the amount of pyridostigmine per pediatric or adult unit form, will advantageously be equivalent to a range of from 0.4 mg to 800 mg, normally from 15 mg to 800 mg, from 30 mg to 800 mg, from 30 mg to 600 mg, from 30 mg to 400 mg, from 30 mg to 200 mg, from 30 mg to 180 mg or from 30 mg to 90 mg, of pyridostigmine bromide, depending on safety and tolerability (per day the dose is equivalent to a range of from 30 mg to 2400 mg (1650 mg-2400 mg and even more in severe MG forms), normally from 30 mg to 1200 mg, from 30 mg to 1080 mg or from 30 mg to 720 mg of pyridostigmine bromide).

The NK1-antagonist Component (a) and pyridostigmine Component (b) can be administered separately or together in any conventional oral or parenteral dosage unit form such as capsule, tablet, powder, cachet, suspension, solution, or transdermal device.

In the case of separate (concurrent or sequential) administration of said NK1-antagonist, in an effective amount per unit form, and of said pyridostigmine, in an effective amount per unit form, each of them can be packaged in a kit comprising said NK1-antagonist, in admixture with a pharmaceutical carrier or vehicle, in a container; and said pyridostigmine, in admixture with a pharmaceutical carrier or vehicle, in another, separate container.

For their concurrent administration for the treatment of symptoms of muscle weakness associated with MG and other myasthenic syndromes, said NK1-antagonist and said pyridostigmine may also be formulated together in fixed-dose combination consisting of a pharmaceutical composition comprising said NK1-antagonist and said pyridostigmine, in admixture with a pharmaceutical carrier or vehicle.

The fixed-dose combinations assure the safe, concurrent administration of the NK1-antagonist and of pyridostigmine.

As set forth above, the amount per unit form of the NK1-antagonist is at least as high as the dose approved for the prevention or treatment of postoperative nausea and vomiting or for the prevention of chemotherapy-induced nausea and vomiting and may be up to 6 times said dose.

Fourth Aspect of the Invention

According to a fourth aspect of the present invention, the pharmaceutical composition comprising a NK1-antagonist may contain another active ingredient, in particular pyridostigmine, co-formulated with said NK1-antagonist, in admixture with a pharmaceutical carrier or vehicle.

Thus, the present invention further provides a fixed-dose combination including a pharmaceutical or veterinary composition in dosage unit form comprising, as active ingredients, Component (a) a NK1-antagonist; and Component (b) pyridostigmine, in admixture with a pharmaceutical carrier or vehicle.

Normally, in said composition, the NK1-antagonist Component (a) is present in an amount per unit form of from 1 µg to 600 mg and the pyridostigmine Component (b) is present in an amount equivalent to from 0.4 mg to 800 mg, from 15 mg to 800 mg, or from 30 mg to 800 mg of pyridostigmine bromide.

Said fixed-dose combination is useful for the treatment of MG and other myasthenic disorders in a mammal such as a cat, a dog or a human being. Said treatment safely provides said mammal with a NK1-antagonist dose of from 1 µg to 600 mg and a single pyridostigmine dose equivalent to from 0.4 mg to 800 mg of pyridostigmine bromide.

When said mammal is a human being, the above fixed-dose combination may be safely used for the treatment of infants, including neonates, and includes pyridostigmine doses for the titration.

Among the above NK1-antagonists to be used in combination, including fixed-dose combinations, with pyridostigmine, aprepitant and pharmaceutically acceptable salts and solvates and prodrugs thereof, rolapitant and pharmaceutically acceptable salts and solvates thereof, netupitant and pharmaceutically acceptable salts and solvates and prodrugs thereof are particularly advantageous.

According to One Embodiment said NK1-antagonist Component (a) active ingredient is selected from the group consisting of aprepitant and pharmaceutically acceptable salts and solvates thereof, in an amount, per unit form, equivalent to from 10 mg to 250 mg of aprepitant; fosaprepitant and pharmaceutically acceptable salts and solvates thereof, in an amount, per unit form, equivalent to from 10 mg to 250 mg of aprepitant;

rolapitant and pharmaceutically acceptable salts and solvates thereof, in an amount, per unit form, equivalent to from 15 mg to 270 mg of rolapitant; netupitant and pharmaceutically acceptable salts and solvates thereof, in an amount, per unit form, equivalent to from 300 mg to 600 mg of netupitant; netupitant-300/palonosetron-0.5; and fosnetupitant-235/palonosetron-0.25;

said pyridostigmine pharmaceutically acceptable salt Component (b) is in an amount per unit form equivalent to a range selected from the group consisting of from 0.4 mg to 800 mg, from 15 mg to 800 mg, from 30 mg to 800 mg, from 30 mg to 600 mg, from 30 mg to 400 mg, from 30 mg to 360 mg, from 30 mg to 270 mg, from 30 mg to 240 mg, from 30 mg to 180 mg and from 30 mg to 90 mg of pyridostigmine bromide; and the Components are mixed together and with a pharmaceutical carrier or vehicle.

In particular, according to this embodiment, said NK1-antagonist Component (a) is selected from the group consisting of aprepitant, in an amount per unit form of from 10 mg to 250 mg; fosaprepitant meglumine, in an amount per unit form equivalent to from 10 mg to 250 mg of aprepitant; or rolapitant, in an amount per unit form of from 15 mg to 270 mg or from 30 mg to 270 mg; and said pharmaceutically acceptable salt of pyridostigmine Component (b) is pyridostigmine bromide, in an amount per unit form of from 0.4 mg to 800 mg, from 15 mg to 800 mg, from 30 mg to 800 mg, from 30 mg to 600 mg, from 30 mg to 400 mg, or from 30 mg to 240 mg.

In the above NK1-antagonist/pyridostigmine fixed dose combinations, including low doses for the use in the titration phase and the treatment of neonates and infants, the above-illustrated pharmaceutical compositions in dosage unit form are preferably administered to a pediatric or adult patient suffering from symptoms of muscle weakness associated with MG or another myasthenic syndrome to provide a pyridostigmine daily dose equivalent to from 0.4 mg to 2400 mg, from 30 mg to 2400 mg, and even more, normally from 270 mg to 1500 mg (up to 1650-2250 mg in severe forms), from 270 mg to 1200 mg, from 270 mg to 1080 mg or from 270 mg to 720 mg of pyridostigmine bromide.

When the NK1-antagonist is aprepitant, the dose/unit form will range from 10 mg to 250 mg.

When the NK1-antagonist is rolapitant, the dose per unit form in combination with pyridostigmine, at the above doses/unit form, will range from 30 mg to 270 mg.

The Formulations

For the use in the treatment of symptoms of muscle weakness associated with MG and other myasthenic syndromes in combination with pyridostigmine, the NK1-antagonist is formulated in a pharmaceutical composition, wherein said NK1-antagonist is in admixture with a pharmaceutical carrier or vehicle. For said treatment, also pyridostigmine is formulated in a pharmaceutical composition, wherein said pyridostigmine is in admixture with a pharmaceutical carrier or vehicle.

Thus, according to one of its additional aspects, the present invention provides pharmaceutical compositions including, as one of their active ingredients, a pharmacologically active amount of a NK1-antagonist as shown above or of one of its pharmaceutically acceptable salts, in mixture with a pharmaceutical carrier or vehicle. As set forth above, the pharmaceutical compositions are formulated in admixture with a pharmaceutical carrier or vehicle for any administration route. For example, said pharmaceutical compositions are in a pharmaceutical dosage unit form for oral, intravenous (including infusion), intramuscular, intranasal, intraperitoneal, subcutaneous, transdermal, or rectal administration, formulated with the classic excipients suitable for said different ways of administration.

Particularly advantageous are the formulations in the form of tablets, multi-score tablets, coated tablets, orally disintegrating tablets, extended release tablets, hard or soft capsules, extended-release capsules, patches for transdermal administration, liquid oral solutions, syrups or suspensions in a predetermined unit form, and vials for the intravenous or subcutaneous administration.

"Transdermal drug delivery system" (TDDS) provides transdermal delivery using transdermal drug formulations and transdermal patches incorporating such transdermal drug formulations. For example, the transdermal drug delivery system may include a composition in form of a patch, a cream, a gel, a lotion or a paste comprising a NK1-antagonist, pyridostigmine or both the active ingredients.

Said unit forms are manufactured according to conventional technologies. Particularly advantageous are the formulations in the form of tablets, multi-score tablets, multi-layer tablets, coated tables, orally disintegrating tablets, extended release tablets, hard or soft capsules, multi-compartment capsules, extended-release capsules, patches for transdermal administration, liquid oral solutions, syrups or suspensions in a predetermined unit form, apparatus for intravenous infusion, and vials for the intravenous or subcutaneous administration.

In the combination of the present invention, the pharmaceutical compositions may be formulated in oral forms such as tablets or gelatin capsules wherein the NK1-antagonist or pyridostigmine or both the active ingredients are in admixture with a carrier or vehicle that may include a diluent, such as cellulose, dextrose, lactose, mannitol, sorbitol or sucrose; a lubricant, such as stearic acid, calcium or magnesium stearate, polyethylene glycol, silica, or talc; and if needed, a binder such as magnesium aluminum silicate, gelatin, methylcellulose, sodium carboxymethylcellulose, or polyvinylpyrrolidone.

Said oral forms may be tablets coated with sucrose or with various polymers; or, alternatively, the tablets can be manufactured by using carriers such as acrylic and methacrylic acid polymers and copolymers; cellulose derivatives such as hydroxypropylethylcellulose; or other appropriate materials, to have a prolonged or delayed activity by progressively releasing a predetermined quantity of NK1-antagonist or of pyridostigmine, or of both the active ingredients. The oral formulations can also be in form of capsules allowing the extended release of the NK1-antagonist, or of pyridostigmine, or of both the active ingredients.

The unit forms may be formulated in tablets in which Component (b) is in Extended Release ("ER")-formulation, for example in admixture with hydroxypropyl methyl cellulose or in a film-coated microgranule. Carriers and vehicles for ER tablets include retardant materials such as acrylic and methacrylic acid polymers and copolymers; the aforementioned cellulose derivatives such as hydroxypropylmethylcellulose, hydroxyethylcellulose, hydroxypropylethylcellulose, hydroxypropylcellulose, methylcellulose, ethylcellulose, or sodium carboxymethylcellulose; gums; waxes; glycerides or aliphatic alcohols or a mixture thereof.

In the combination of the present invention, each unit form may also be a vial containing the pharmaceutical composition a solution, an emulsion, a powder for reconstitution or also an apparatus for continuous infusion of a solution or an emulsion, wherein the active ingredient is dissolved in or mixed with a pharmaceutical carrier for parenteral use.

The pharmaceutical compositions may also be formulated in a TDDS, such as a patch formulation wherein the active ingredient or the mixture of the active ingredients, for example in a matrix, may comprise adjuvants such as D-sorbitol, gelatin, kaolin, methyl paraben, polysorbate 80, propylene glycol, propyl paraben, povidone, sodium carboxymethylcellulose, sodium polyacrylate, tartaric acid, titanium dioxide, and purified water. A patch formulation may also contain skin permeability enhancer such as lactate esters (e.g., lauryl lactate), triacetin or diethylene glycol monoethyl ether.

A useful pharmaceutical composition according to the present invention is formulated in a liquid formulation, such, as a syrup, wherein Component (b) is dissolved in admixture with a pharmaceutical carrier. A typical syrup will contain an amount of from 30 mg/5 ml to 60 mg/5 ml of pyridostigmine bromide.

In the above pharmaceutical compositions, the preferred NK1-antagonist active ingredient is aprepitant, fosaprepitant, rolapitant, netupitant-300/palonosetron-0.5; or fosnetupitant-235/palonosetron-0.25, and the preferred pyridostigmine is pyridostigmine bromide.

When the NK1-antagonist and pyridostigmine are in a fixed-dose combination for oral administration, the unit form may be a stratified, bi-layer tablet wherein the NK1-antagonist, formulated with a pharmaceutical carrier, normally in IR-formulation, is in one of the layers and pyridostigmine, formulated with a pharmaceutical carrier, is the other layer, preferably in ER-formulation. Similarly, the NK1-antagonist and pyridostigmine active ingredients are in a pill containing one of the active ingredients, admixed with a pharmaceutical carrier, in the core and the other active ingredient, admixed with a pharmaceutical carrier, is in the outer part of the pill, the core and the outer part being optionally separated by an inert film or carrier. Analogously, capsules made of two separated parts, one containing Component (a), in IR-formulation and the other containing Component (b), in ER-formulation, may be manufactured.

In the case of mammals such as cats and dogs and of human pediatric or obese human patients, the NK1-antagonist daily dose may be decided on the basis of the body weight. Thus, for example, aprepitant may be administered at a daily dose of 0.16 mg/kg to 4.2 mg/kg and rolapitant may be administered at a daily dose of 0.25 mg/kg to 4.5 mg/kg. As set forth above, pyridostigmine is administered at a daily dose of from 0.05 mg/kg to 6 mg/kg of body weight of pyridostigmine bromide.

Kits

The present invention also provides a kit or package containing a medicament, a pharmaceutical combination, or a pharmaceutical composition as described herein, accompanied by instructions for use of the same in the treatment of symptoms of muscle weakness associated with myasthenia gravis or another myasthenic syndrome in a mammalian subject in need thereof.

In one embodiment, a kit of the present invention is a kit comprising a combination of a NK1-antagonist and pyridostigmine, formulated together in a pharmaceutical composition, in admixture with a pharmaceutical carrier or vehicle; and instructions for use of the same for treatment of symptoms of muscle weakness associated with myasthenia gravis or another myasthenic syndrome in a mammalian subject in need thereof.

In another embodiment, a kit of the present invention is a kit comprising pharmaceutical composition (a) comprising a NK1-antagonist and pharmaceutical composition (b) comprising pyridostigmine; and instructions for use of the same for treatment of symptoms of muscle weakness associated with myasthenia gravis or another myasthenic syndrome in a mammalian subject in need thereof.

The foregoing detailed description has been given for illustration purposes only, especially for purposes of clarity of understanding. The description is not meant to be construed in a limiting sense. It will be apparent to those skilled in the art that certain changes and modifications of the disclosed embodiments as well as alternative embodiments may be practiced without departing from the spirit and scope of the invention. It is contemplated that the appended claims will cover any such modifications or embodiments that fall within the scope of the invention.

Example 1

The ability of the NK1-antagonists for preventing the adverse effects of pyridostigmine bromide in humans is tested.

A Phase I study is conducted in human subjects receiving a single oral dose of pyridostigmine bromide with or without a single oral dose of aprepitant, as a representative NK1-antagonist. The study was a single center, single-blind, placebo-controlled study.

The objective of the study is to demonstrate that aprepitant could safely attenuate the gastro-intestinal side effects of pyridostigmine given in doses demonstrated to be effective for the treatment of Myasthenia Gravis.

To be enrolled in the study, participants are to meet the following inclusion/ex elusion criteria:

Key Inclusion Criteria

1. Male or female volunteers between the ages of 18 and 60 years inclusive are required to be in good health, to refrain from consuming xanthine, quinine and caffeine containing beverages, and to refrain from prolonged intensive physical exercise during the study conduct.
2. Subjects are to sign an informed consent form indicating that they understand the purpose of and procedures for the study and that they are willing to participate in the study and comply with the study procedures and restrictions.
3. Subjects had to be in good health according to their medical history including personal and family psychiatric history, physical examination, ECG, vital signs, and laboratory tests. A subject with a medical abnormality could be included only if the investigator or designee considers that the abnormality does not introduce significant additional risk to the subject's health or interfere with study objectives.
4. Subjects had to be able to swallow multiple pills simultaneously.

Key Exclusion Criteria

1. Any clinically relevant acute or chronic disease which could interfere with the subjects' safety during the trial, expose them to undue risk, or interfere with the study objectives.
2. History or presence of gastrointestinal, hepatic, or renal disease or other condition known to interfere with the absorption, distribution, metabolism or excretion of drugs.
3. History of substance abuse, known drug addiction, or positive test for drugs of abuse or alcohol.
4. History of drug or other significant allergy.
5. ECG changes including QT interval prolongation and congenital long QT syndrome. Electrolyte abnormalities (e.g., hypokalemia or hypomagnesemia), congestive heart failure, bradyarrhythmias or other conditions that lead to QT prolongation.
6. Treatment with centrally active drugs or those affecting peripheral cholinergic transmission within 3 months of study entry.

7. Smokers (except subjects who stopped smoking 1 year or more before enrollment in the Study).
8. Excessive daily consumption of xanthines containing drinks (i.e. >500 mg/day of caffeine).
9. Intake of an investigational drug within 30 days of study entry.

Following enrollment in the study, participants will receive single increasing oral doses of pyridostigmine, given once daily in the morning. Once a subject reaches his/her first intolerable dose ("FID-1"), upward dose escalation is discontinued. FID is defined as:
(a) one episode of vomiting; or
(b) two episodes of retching; or
(c) one episode of severe nausea (Grade 3; defined as nausea interfering with activities of daily living or inadequate oral caloric or fluid intake; tube feeding, total parenteral nutrition or hospitalization indicated) lasting more than 1 hour; or
(d) one episode of moderate diarrhea (Grade 2); defined as 4-6 stools more than at baseline); or
(e) three (3) consecutive episodes at every 4 hour ratings of moderate nausea (Grade 2; defined as subjectively symptomatic, but not interfering with activities of daily living).

When a subject reaches FID-1 on pyridostigmine alone, the subject is washed out for 2 to 7 days, and then receives their first intolerable dose (FID) of pyridostigmine plus a single oral dose of aprepitant, (in doses of aprepitant up to 125 mg to prevent dose-limiting adverse events) or aprepitant placebo.

On each study day, subjects are followed up for up to 8 hours for AEs, vital signs, ECGs. In addition, a laboratory panel at screening and at the end of the study is taken.

The co-administration of oral high dose aprepitant with pyridostigmine prevents or attenuates the occurrence of gastro-intestinal AEs with pyridostigmine given in doses at least as high as or much higher than the currently recommended efficacious dose of pyridostigmine for the treatment of myasthenia gravis.

REFERENCES

Abicht A, Müller J S, Lochmüller H. Congenital Myasthenic Syndromes. In: Pagon R A, Adam M P, Ardinger H H, Wallace S E, Amemiya A, Bean L J H, Bird T D, Ledbetter N, Mefford H C, Smith R J H, Stephens K, editors. GeneReviews® [Internet]. Seattle (Wash.): University of Washington, Seattle; 1993-2016. 2003 May 9 [updated 2016 Jul. 14].
Drachman D B. Myasthenia Gravis. Semin Neurol. 2016; 36:419-424. Epub 2016 Sep. 23.
Engel A G. Congenital Myasthenic Syndromes in 2012. Curr. Neurol Neurosci Rep, 2012; 12:92-101.
Gotterer L, Li Y. Maintenance immunosuppression in myasthenia gravis. J Neurol Sci. 2016; 369:294-302. Epub 2016 Aug. 28.
Howard J. F. Clinical Overview of MG. Myasthenia Gravis Foundation of America; 2015.
O'Grady G L, Verschuuren C, Yuen M, Webster R, Menezes M, Fock J M, Pride N, Best H A, Benavides Damm T, Turner C, Lek M, Engel A G, North K N, Clarke N F, MacArthur D G, Kamsteeg E J, Cooper S T. Variants in SLC18A3, vesicular acetylcholine transporter, cause congenital myasthenic syndrome. Neurology. 2016; 87: 1442-1448. Epub 2016 Sep. 2.
Phillips WD1, Vincent A2. Pathogenesis of myasthenia gravis: update on disease types, models, and mechanisms. F1000Res. 2016; 27:5.
Shelton G D I. Myasthenia gravis and congenital myasthenic syndromes in dogs and cats: A history and mini-review. Neuromuscul Disord. 2016; 26: 331-334. Epub 2016 Mar. 10.
Smith S V, Lee A G. Update on Ocular Myasthenia Gravis. Neurol Clin. 2017; 35: 115-123.

ASPECTS OF THE INVENTION

1. A method for safely improving the conditions of a mammal suffering from symptoms of muscle weakness associated with MG or another myasthenic syndrome, comprising chronically administering to said mammal a NK1-antagonist in combination with pyridostigmine;
2. The method of aspect 1, wherein said pyridostigmine is pyridostigmine bromide;
3. The method of aspect 1, wherein said NK1-antagonist is aprepitant or a pharmaceutically acceptable salt or solvate or prodrug thereof;
4. The method of aspect 1, wherein said NK1-antagonist is administered to said mammal at a single oral or subcutaneous dose of from 1 µg to 600 mg/day;
5. The method of aspect 1, wherein said pyridostigmine in said combination is administered to said mammal at a single oral dose equivalent to from 0.5 mg/kg to 6 mg/kg of pyridostigmine bromide;
6. The method according to aspect 1, wherein said pyridostigmine in said combination is administered to said mammal in a unit form comprising an amount per unit form of said pyridostigmine equivalent to from 0.4 mg to 800 mg of pyridostigmine bromide;
7. The method according to aspect 1, wherein said pyridostigmine in said combination is administered to said mammal at a single subcutaneous dose equivalent to from 0.1 mg/kg to 1.2 mg/kg of pyridostigmine bromide;
8. The method according to aspect 1, wherein said pyridostigmine in said combination is administered to said mammal at a daily continuous infusion subcutaneous dose equivalent to from 0.5 mg/kg to 4 mg/kg of pyridostigmine bromide;
9. The method according to aspect 3, wherein said prodrug of said aprepitant is fosaprepitant;
10. The method according to aspect 1, wherein the mammal is suffering from myasthenia gravis;
11. The method according to aspect 10, wherein the mammal is a human, dog or cat;
12. The method according to aspect 11, wherein the mammal is a human;
13. The method according to aspect 1, wherein said NK1-antagonist and said pyridostigmine are in a fixed-dose combination comprising a pharmaceutical or veterinary composition in dosage unit form comprising, as active ingredients, Component (a) a NK1-antagonist; and Component (b) pyridostigmine, in admixture with a pharmaceutical carrier or vehicle;
14. The method according to aspect 13, wherein the NK1-antagonist Component (a) is present in said composition an amount per unit form of from 1 µg to 600 mg and the pyridostigmine Component (b) is present in said composition in an amount equivalent to of from 0.4 mg to 800 mg of pyridostigmine bromide;
15. A method for treating a myasthenic syndrome, comprising administering to a mammalian subject, in need thereof, an effective daily dose of a combination comprising an NK1-antagonist and pyridostig mine;
16. A fixed-dose combination comprising a pharmaceutical or veterinary composition in dosage unit form comprising, as active ingredients, Component (a) a NK1-antagonist; and Component (b) pyridostigmine, in admixture with a pharmaceutical carrier or vehicle;

17. The fixed-dose combination of aspect 16, wherein the NK1-antagonist Component (a) is present in an amount per unit form of from 1 μg to 600 mg and the pyridostigmine Component (b) is present in an amount equivalent to of from 0.4 mg to 800 mg of pyridostigmine bromide or pyridostigmine methylsulfate;

18. A pharmaceutical combination comprising an NK1-antagonist and pyridostigmine;

19. The composition of aspect 18, further comprising a pharmaceutically acceptable carrier or vehicle; and 20. A kit comprising the pharmaceutical combination of aspect 18, or the pharmaceutical composition of aspect 19, and instructions for treatment of symptoms of muscle weakness associated with myasthenia gravis or another myasthenic syndrome.

The invention claimed is:

1. A method for improving muscle weakness in a mammal suffering from myasthenia gravis or another myasthenic syndrome, comprising chronically administering to said mammal a neurokinin 1 (NK1)-antagonist in combination with an oral dose of pyridostigmine bromide, wherein the daily amount of pyridostigmine bromide administered to the mammal is greater than 1500 mg/day up to the maximally effective daily dose.

2. The method of claim 1, wherein the mammal is a human.

3. The method of claim 2, wherein said NK1-antagonist is administered to said mammal at a single oral or subcutaneous dose of from 1 μg to 600 mg/day.

4. The method of claim 3, wherein said NK1-antagonist and said pyridostigmine are in a fixed-dose combination comprising a pharmaceutical composition in dosage unit form comprising an NK1-antagonist and pyridostigmine in admixture with a pharmaceutical carrier or vehicle.

5. The method of claim 4, wherein said NK1-antagonist is aprepitant or a pharmaceutically acceptable salt or solvate or prodrug thereof.

6. The method of claim 5, wherein said prodrug of said aprepitant is fosaprepitant.

7. The method of claim 1, wherein the total daily oral dosage of pyridostigmine bromide is between 1500 mg and 2400 mg.

8. The method of claim 1, wherein the total daily oral dosage of pyridostigmine bromide is between 1650 mg and 2400 mg.

* * * * *

UNITED STATES PATENT AND TRADEMARK OFFICE
CERTIFICATE OF CORRECTION

| | |
|---|---|
| PATENT NO. | : 11,752,141 B2 |
| APPLICATION NO. | : 16/752590 |
| DATED | : September 12, 2023 |
| INVENTOR(S) | : Kathleen Clarence-Smith |

It is certified that error appears in the above-identified patent and that said Letters Patent is hereby corrected as shown below:

On the Title Page

Item (54) In the Title and In the Specification, Column 1, Lines 1-4, should read:
PHARMACEUTICAL COMPOSITIONS AND METHODS UTILIZING PYRIDOSTIGMINE AND AN NK-1 ANTAGONIST FOR TREATING MYASTHENIA GRAVIS Signed and Sealed this
Twelfth Day of November, 2024

*Katherine Kelly Vidal*

Katherine Kelly Vidal
*Director of the United States Patent and Trademark Office*